United States Patent [19]

Nohira et al.

[11] Patent Number: 5,852,209
[45] Date of Patent: Dec. 22, 1998

[54] PROCESS FOR OPTICALLY RESOLVING 2-(3-BENZOYLPHENYL) PROPIONIC ACID

[75] Inventors: Hiroyuki Nohira, Urawa; Shigeya Saijo, Nishinomiya; Masafumi Moriwaki, Kobe; Shunji Kamiyama, Kobe; Kazutoshi Toyoda, Kobe; Jun Matsumoto, Kobe; Kohichi Maruo, Akashi; Taizo Fujimoto, Osaka, all of Japan

[73] Assignee: Nagase & Co., Ltd., Osaka, Japan

[21] Appl. No.: 897,500

[22] Filed: Jun. 9, 1997

Related U.S. Application Data

[63] Continuation of Ser. No. 413,869, Mar. 29, 1995, abandoned.

[30] Foreign Application Priority Data

Sep. 26, 1994 [JP] Japan ..................................... 6-229362
Jan. 24, 1995 [JP] Japan ..................................... 7-008908

[51] Int. Cl.$^6$ ..................................................... C07B 57/00
[52] U.S. Cl. .............................................................. 562/401
[58] Field of Search .............................................. 562/401

[56] References Cited

U.S. PATENT DOCUMENTS

| | | | |
|---|---|---|---|
| 3,641,127 | 2/1972 | Farge et al. | 260/516 |
| 4,983,765 | 1/1991 | Lukas et al. | 562/460 |
| 5,162,576 | 11/1992 | Manimaran et al. | 562/401 |
| 5,191,112 | 3/1993 | Nohira et al. | 562/401 |
| 5,321,154 | 6/1994 | Nohira | 562/401 |

FOREIGN PATENT DOCUMENTS

| | | | |
|---|---|---|---|
| 0423467 | 4/1991 | European Pat. Off. | C07C 59/84 |
| 0 529 835A3 | 3/1993 | European Pat. Off. | C07C 57/30 |
| 2-289536 | 11/1990 | Japan | C07C 59/84 |
| 93-17677 | 9/1993 | WIPO | A61K 31/19 |

*Primary Examiner*—Gary Geist
*Assistant Examiner*—Jean F. Vollano
*Attorney, Agent, or Firm*—Jacobson, Price, Holman & Stern, PLLC

[57] ABSTRACT

Provided is a process for separating (S)- or (R)-2-(3-benzoylphenyl)propionic acid from a mixture of (S)- and (R)-2-(3-benzoylphenyl)propionic acid, which comprises (1) reacting the mixture of (S)- and (R)-2-(3-benzoylphenyl) propionic acid with (S)- or (R)-3-methyl-2-phenylbutylamine in a suitable solvent to form a diastereomer salt of (S)-2-(3-benzoylphenyl)propionic acid with (S)-3-methyl-2-phenylbutylamine or a diastereomer salt of (R)-2-(3-benzoylphenyl)propionic acid with (R)-3-methyl-2-phenylbutylamine; (2) separating the diastereomer salt from the reaction mixture; and (3) liberating the separated diastereomer salt to give (S)- or (R)-2-(3-benzoylphenyl) propionic acid. According to the present process, it is possible to obtain optically active (S)- or (R)-2-(3-benzoylphenyl)propionic acid having 99% or more of high optical purity in a high yield. Thus, the present process is a practical and efficient process which can simplify purification steps and can be applied for an industrial production process.

14 Claims, No Drawings

PROCESS FOR OPTICALLY RESOLVING 2-(3-BENZOYLPHENYL) PROPIONIC ACID

This application is a continuation of application Ser. No. 08/413,869, filed Mar. 29, 1995, now abandoned.

FIELD OF THE INVENTION

The present invention relates to a process for producing (S)- and (R)-2-(3-benzoylphenyl)propionic acid, which are optically pure for pharmaceutical use, by optical resolution of a mixture of (S)- and (R)-2-(3-benzoylphenyl)propionic acid using (S)- and (R)-3-methyl-2-phenylbutylamine, respectively, as an optical resolution agent. The present process is particularly useful for an industrial production of the optically active 2-(3-benzoylphenyl)propionic acid.

PRIOR ART 2-(3-Benzoylphenyl)propionic acid is referred to as ketoprofen and is applied for practical use as a non-steroidal antiphlogistic analgesic. In this compound, it is known that a physiological activity of (S)-ketoprofen is more effective than that of (R)-ketoprofen (H. Fujimura, Pharmacia, Vol. 11, No. 7, p.p. 515–518, 1975). Thus, (R)-ketoprofen is unnecessary in the preparation of a pharmaceutical formulation, and furthermore, there is some fear that the (R)-isomer causes a side effect. Accordingly, there is a need for optically pure (S)-2-(3-benzoylphenyl)propionic acid substantially free from (R)-ketoprofen. Also, a practical industrial process for producing (S)-ketoprofen has been strongly needed.

As described above, it has been known that the effect as an antiphlogistic analgesic is present only in the S-isomer and not in the R-isomer. Recently, however, it has been observed that (R)-ketoprofen has an effect as an analgesic when used in a manner different from that used for (S)-ketoprofen. In particular, it has been reported that the (R)-ketoprofen is effective as a therapeutic agent for toothache, etc., and has a little side effect (International Application Publication No. WO 93/17677). Thus, it has recently been recognized that each of S-isomer and R-isomer of ketoprofen has a distinct and separate use. Accordingly, there is a significant need for a practical process for the industrial production of not only S-isomer, but also the R-isomer, which have high optical purity and can be used as a drug.

As a process for producing (S)-2-(3-benzoylphenyl)propionic acid having high optical purity by optical resolution of 2-(3-benzoylphenyl)propionic acid, for example, a process using phenylethylamine as an optical resolution agent (Lukas et al., U.S. Pat. No. 4,983,765), a process using an optically active amine, such as phenylpropylamine as in optical resolution agent (Nohira et al., U.S. Pat. No. 5,191,112, Japanese Patent Publication (Kokai) No. 289536/1990), and a process using cinchonidine as an optical resolution agent (Manimaran et al., U.S. Pat. No. 5,162,576) have been known hitherto.

However, the process of Lukas et al. has a low yield (40%), although they do not disclose their process in detail. In the process of Nohira et al., about one equivalent of the optical resolution agent is used on the basis of the racemic compound used, and the product having an optical purity of 99% or more is obtained through a purification process by two or more recrystallizations. However, the yield of this process is relatively low. In the process of Manimaran et al., (S)-ketoprofen is obtained in a relatively high yield (62%) by using a mixed solvent of a fatty acid ester and alcohol as a solvent and using purification by a single recrystallization, but the optical purity is relatively low (97%). Accordingly, an additional purification process is often needed in order to obtain an optical purity of 98% or more, preferably 99% or more, which is required for use as a drug. Furthermore, the process needs to use about one equivalent of cinchonidine and provides only S-isomer as a product having a high optical purity because cinchonidine is used, and there is no disclosure as to a process for producing the R-isomer. As described above, the known processes have a number of problems to be solved from the viewpoint of an industrial production process.

Accordingly, the object of the present invention is to solve the above problems and to provide optically active ketoprofen (S-isomer, R-isomer) having a high optical purity of 98% or more, preferably 99% or more, in a high yield, which can be applied to practical use as a drug. In particular, the object of the present invention is to provide a practical process which needs only a simple purification step and can be applied for an industrial production process.

BRIEF DESCRIPTION OF THE INVENTION

The present inventors intensively studied in order to solve the above problems and found that, when optically active (S)-3-methyl-2-phenylbutylamine or (R)-3-methyl-2-phenylbutylamine is used as an optical resolution agent in optical resolution of 2-(3-benzoylphenyl)propionic acid, it is possible to obtain, in a high yield, (S)-2-(3-benzoylphenyl)propionic acid or (R)-2-(3-benzoylphenyl)propionic acid, which has an extremely high optical purity of 98% or more, furthermore 99% or more, and which can be used as a drug, without purifying the formed diastereomer salt by recrystallization, or by purifying it by only a single recrystallization. The present invention was thus accomplished.

That is, the present invention provides a process for separating (S)-2-(3-benzoylphenyl)propionic acid or (R)-2-(3-benzoylphenyl)propionic acid from a mixture of (S)- and (R)-2-(3-benzoylphenyl)propionic acid, which comprises the steps of:

(1) reacting the mixture of (S)- and (R)-2-(3-benzoylphenyl)propionic acid with (S)- or (R)-3-methyl-2-phenylbutylamine in a solvent to form a diastereomer salt of (S)-2-(3-benzoylphenyl)propionic acid with (S)-3-methyl-2-phenylbutylamine or a diastereomer salt of (R)-2-(3-benzoylphenyl)propionic acid with (R)-3-methyl-2-phenylbutylamine;

(2) separating the diastereomer salt from the reaction solution; and (3) liberating the separated diastereomer salt to give (S)-2-(3-benzoylphenyl)propionic acid or (R)-2-(3-benzoylphenyl)propionic acid.

DETAILED DESCRIPTION OF THE INVENTION

The process of the present invention is further illustrated in detail.

(S)-3-Methyl-2-phenylbutylamine and (R)-3-methyl-2-phenylbutylamine used in the process of the present invention can be produced according to the process described in Japanese Patent Publication (Kokai) No. 172853/1986. That is, benzyl cyanide and isopropyl bromide are reacted with triethylbenzylammonium chloride in 50% (w/v) of aqueous NaOH solution to give 2-phenylisobutyl cyanide. This compound is reduced by reacting with lithium aluminum hydride to give (±)-3-methyl-2-phenylbutylamine. Then, optical resolution is conducted using optically active mandelic acid to give optically active (S)-3-methyl-2-phenylbutylamine and (R)-3-methyl-2-phenylbutylamine.

Optical resolution of a mixture of (S)- and (R)-2-(3-benzoylphenyl)propionic acid can be conducted as follows.

Firstly, the mixture of (S)- and (R)-2-(3-benzoylphenyl) propionic acid is dissolved in a suitable solvent. Examples of the suitable solvent include ketones, such as acetone, methyl ethyl ketone, diethyl ketone or methyl isobutyl ketone; carboxylates, such as ethyl acetate, propyl acetate or methyl propionate; alcohols, such as methyl alcohol, ethyl alcohol or isopropyl alcohol; ethers, such as methyl-t-butyl ether, diisopropyl ether, dipropyl ether, dibutyl ether, tetrahydrofuran, tetrahydropyran or dioxane; aromatic hydrocarbons, such as toluene or xylene; or a mixture thereof. Preferred solvents are ketones and ethers, and more preferred solvents are ethers.

To this solution, (S)-3-methyl-2-phenylbutylamine [or (R)-3-methyl-2-phenylbutylamine] is added to form a diastereomer salt of (S)-2-(3-benzoylphenyl)propionic acid with (S)-3-methyl-2-phenylbutylamine [or (R)-2-(3-benzoylphenyl)propionic acid with (R)-3-methyl-2-phenylbutylamine].

The mixture of (S)-2-(3-benzoylphenyl)propionic acid and (R)-2-(3-benzoylphenyl)propionic acid used herein may be a mixture having any ratio. Commonly, a mixture having the ratio of 1:1, i.e. racemic mixture is often used. The amount of (S)-3-methyl-2-phenylbutylamine [or (R)-3-methyl-2-phenylbutylamine] to be added may be about one equivalent, preferably 0.8 to 1.5 equivalents, more preferably 0.9 to 1.2 equivalents, based on the amount of (S)-2-(3-benzoylphenyl)propionic acid [or (R)-2-(3-benzoylphenyl)propionic acid] contained in the mixture.

In the known processes described above, about one equivalent of an optical resolution agent is used on the basis of the amount of (±)-2-(3-benzoylphenyl)propionic acid, that is, about 2 equivalents on the basis of the amount of (S)-2-(3-benzoylphenyl)propionic acid contained in (±)-2-(3-benzoylphenyl)propionic acid. In the process of the present invention, only about half that amount of the optical resolution agent is required, and therefore, an efficient optical resolution can be accomplished using a smaller amount of the optical resolution agent. Furthermore, when using the optical resolution agent in the process of the present invention, the optical purity and the yield of a diastereomer salt to be formed can be adjusted by the amount of the agent, as shown in Examples described hereinafter. Accordingly, it is possible to set an optimum process for producing (S)-2-(3-benzoylphenyl)propionic acid having a desired optical purity in a good yield.

Furthermore, the present inventors found that a much better optical purity and yield can be accomplished by adding water to a reaction system in an amount of 10 to 60% (w/w), preferably 20 to 55% (w/w), based on the amount of a mixture of (S)-2-(3-benzoylphenyl)propionic acid and (R)-2-(3-benzoylphenyl)propionic acid. That is, in the preferred embodiment of the present invention, water is added to the reaction system in the above-described amount.

The reaction of forming a diastereomer salt is usually conducted by stirring the reaction solution at a temperature between room temperature and 70° C., preferably between room temperature and 40° C.

The separation of the diastereomer salt may be conducted by a conventional physical means, such as filtration, centrifugation and the like. Usually, a crystal is precipitated by cooling the reaction solution to a suitable temperature (e.g. 10° C. to 15° C.) and adding a seed crystal (if necessary), and the resulting crystal is then filtered off.

The diastereomer salt thus separated can be liberated by a conventional liberation procedure, for example, by adding a mineral acid, such as hydrochloric acid or sulfuric, acid without purifying the salt. Then, the liberated materials can be extracted and separated with a suitable organic solvent, such as ethyl acetate, chloroform, or benzene, to give pharmaceutically acceptable (S)-2-(3-benzoylphenyl) propionic acid [or (R)-2-(3-benzoylphenyl)propionic acid] having a high optical purity.

Alternatively, the above (S)-isomer can be obtained by adding a strong base, such as NaOH, to the diastereomer salt, extracting and removing (S)-3-methyl-2-phenylbutylamine with a suitable solvent, adding an acid, such as hydrochloric acid or sulfuric acid in order to liberate (S)-2-(3-benzoylphenyl)propionic acid, and then extracting and separating the (S)-isomer with the above solvent.

According to a simpler process, the above (S)-isomer can be obtained by adding the diastereomer salt to an aqueous solution of hydrochloric acid or sulfuric acid, precipitating liberated (S)-2-(3-benzoylphenyl)propionic acid [or (R)-2-(3-benzoylphenyl)propionic acid] as a crystal from the aqueous solution without extracting it with a solvent, and then filtering the crystal.

Furthermore, the diastereomer salt can be purified by recrystallization from a solvent, for example, alcohol, such as isopropyl alcohol, water or a mixed solvent thereof, or ketone, such as methyl isobutyl ketone or methyl ethyl ketone (normally, a simple recrystallization is sufficient for purification ). Then, the purified salt can be liberated by the above liberation procedure to give (S)-2-(3-benzoylphenyl) propionic acid having a much higher optical purity. Preferred solvents for recrystallization are ketones, such as methyl isobutyl ketone or methyl ethyl ketone, in view of purification yield. Furthermore, when the recrystallization is conducted using the same solvent as that used in the diastereomer formation reaction (e.g. methyl isobutyl ketone), the filter cake of the crude diastereomer salt can be used for recrystallization as it is without drying it, and therefore, such a procedure is preferred in view of its simplicity.

The advantages of the present process lie in the fact that a product having a high optical purity of 98% or more can be obtained at the stage of a diastereomer salt, and therefore, purification steps, such as recrystallization can be perfectly eliminated. When the purification through recrystallization is conducted, a product having an extremely high optical purity of normally 99% or more, occasionally 99.5% or more can be obtained in a high yield through only a simple recrystallization step, and an additional purification step is not required.

The results obtained by optically resolving (±)-2-(3-benzoylphenyl)propionic acid using various optical resolution agents according to known processes and the present process are shown in Table 1. As is apparent from Table 1, the present process is superior to the known processes in the amount of optical resolution agent used, the number of recrystallizations, yield and optical purity. In Table 1, 2-(3-benzoylphenyl)propionic acid and 3-methyl-2-phenylbutylamine are abbreviated to "KET" and "PBA", respectively.

TABLE 1

| Optical resolution agent | Molar ratio Optical resolution agent/(±)-KET | Reaction solvent | Number of times of recrystallization | Yield of KET (%) | Optical purity of KET (% e.e.) |
| --- | --- | --- | --- | --- | --- |
| a. PPA | 1.0 | Ethyl acetate | 2 | 44 | >99 |
| b. MTBA | 1.0 | Isopropyl alcohol | 1 | 45 | 69 |
| c. Cinchonidine | 0.9 | Ethyl acetate +Methyl alcohol | 1 | 57 | 97 |
| d. Cinchonidine | 1.0 | Methyl isobutyl ketone | 0 | 66.4 | 76.5 |
| e. PBA | 0.5 | Methyl isobutyl ketone | 1 | 55.2 | 99.7 |
| f. PBA | 0.45 | Methyl isobutyl ketone | 0 | 55 | 98.6 |
| g. PBA | 0.6 | Methyl isobutyl ketone | 1 | 71.6 | 99.2 | a: PPA = 1-Phenylpropylamine, Japanese Patent Publication (Kokai) No. 289536/1990
b: MTBA = 2-(4-Methylphenyl)-3-methylbutylamine, Japanese Patent Publication (Kokai) No. 289536/1990
c: Cinchonidine = (8α, 9R)-Cinchonane-9-ol, U.S. Pat. No. 5,162,576
d: Japanese Patent Publication (Kohyo) No. 501683/1994
e: Example 1
f: Example 2
g: Example 7

The process described above can be applied to the production of (R)-isomer in the same manner. Thus, (R)-2-(3-benzoylphenyl)propionic acid having a high optical purity can be obtained using (R)-3-methyl-2-phenylbutylamine in place of (S)-3-methyl-2-phenylbutylamine.

As described above, 2-(3-benzoylphenyl)propionic acid to be resolved by the present process is not limited to racemate but any mixture of (S)-2-(3-benzoylphenyl) propionic acid and (R)-2-(3-benzoylphenyl)propionic acid may be used. For example, starting from 2-(3-benzoylphenyl)propionic acid rich in (R)-isomer or 2-(3-benzoylphenyl)propionic acid rich in (S)-isomer recovered from the solution obtained after removing the diastereomer salt in the above step (2) and applying the optical resolution steps described above, (R)-2-(3-benzoylphenyl)propionic acid or (S)-2-(3-benzoylphenyl)propionic acid having a high optical purity can be also obtained in a still higher yield.

Furthermore, when only the (S)-isomer is desired, 2-(3-benzoylphenyl)propionic acid rich in (R)-isomer, obtained after separating the (S)-isomer, may be racemized by a suitable method, and the (S)-isomer may then be obtained from this racemic mixture. An example of such process is described in Reference Example 1 below.

Also, a product having a high optical purity can be easily obtained by applying the present process to a mixture of the (S)-isomer and the (R)-isomer which is obtained by a process other than that of the present invention, e.g. optical resolution with an enzyme, asymmetric synthesis and the like.

EXAMPLES

The following Examples further illustrate the present invention but should not be construed as a limitation thereof. In the Examples, the optical purity of 2-(3-benzoylphenyl) propionic acid was measured by high performance liquid chromatography (hereinafter abbreviated to "HPLC") under the following analytical conditions. The measuring method of the optical purity is not limited to the following method and it is possible to conduct it by other methods normally known in the art. HPLC conditions are as follows.

Column: CHRALCEL OJ (manufactured by Daiseru Kagaku Kogyo Co., Ltd.)
Mobile phase: hexane/isopropyl alcohol/trifluoroacetic acid (92/8/0.3)
Flow rate: 1.0 ml/min.
Detection: UV, 255 nm
Column temperature: ordinary temperature The optically active 3-methyl-2-phenylbutylamine used in the Examples are those having the following optical purity and rotation.

(S)-(+)-3-methyl-2-phenylbutylamine: 98.4% e.e.; $[\alpha]_D^{25}$=+2.82° (neat)

(R)-(−)-3-methyl-2-phenylbutylamine: 99.2% e.e.; $[\alpha]_D^{25}$=−2.88° (neat)

The optical purity of the above optically active 3-methyl-2-phenylbutylamine was measured by HPLC under the following analytical conditions. The measuring method of the optical purity is not limited to the following method and it is possible to conduct it by other method normally known in the art. HPLC conditions are as follows.

Column: CROWNPAK CR (+) (manufactured by Daiseru Kagaku Kogyo Co., Ltd.)
Mobile phase: methyl alcohol/0.1N aqueous perchloric acid solution (15/85)
Flow rate: 0.8 ml/min.
Detection: UV, 210 nm
Column temperature: ordinary temperature

Example 1

(±)-2-(3-Benzoylphenyl)propionic acid (20.3 g, 80 mmol) was dissolved in methyl isobutyl ketone (hereinafter abbreviated to "MIBK") (90 g) with heating. Then, (S)-(+)-3-methyl-2-phenylbutylamine (6.68 g, 41 mmol) was added dropwise with stirring at 40° C. After completing the addition, the reaction solution was stirred at 40° C. for one hour and then cooled slowly to 10° C. over 6 hours. After stirring at 10° C. for 3 hours, the precipitated crystal was filtered and the filter cake was washed with cold MIBK (50 ml) and then dried. In this manner, a diastereomer salt (11.5 g) of (S)-(+)-2-(3-benzoylphenyl)propionic acid with (S)-(+)-3-methyl-2-phenylbutylamine was obtained.

This diastereomer salt was recrystallized from isopropyl alcohol (hereinafter abbreviated to "IPA") (115 ml). That is, the diastereomer salt was dissolved with heating and then cooled to 10° C. with stirring over 2 hours, followed by stirring at 10° C. for additional 2 hours. Then, the crystal precipitated was filtered, and the filter cake was washed with cold IPA (40 ml) and dried to give a purified diastereomer salt (9.8 g). Melting point: 134.5–135.5° C.

To this purified diastereomer salt, 15% (w/v) hydrochloric acid (30 g) was added and the mixture was stirred for a while. Then, (S)-(+)-2-(3-benzoylphenyl)propionic acid liberated was extracted with ethyl acetate, and the extract solution was washed with water and dried over magnesium sulfate. The solvent was distilled off under reduced pressure, and hexane was then added to allow crystallization. After cooling, the crystal was filtered and dried to give (S)-(+)-2-(3-benzoylphenyl)propionic acid (5.6 g). The yield of the product based on (S)-(+)-2-(3-benzoylphenyl)propionic acid contained in the starting material was 55.2% and the optical purity was 99.7% e.e. Melting point: 77°–78.5° C. $[\alpha]_D^{25}$=+45.7°(c=1, methyl alcohol).

Example 2

(±)-2-(3-Benzoylphenyl)propionic acid (13.55 g, 53.3 mmol) was dissolved in MIBK (67.5 g) with heating. Then, (R)-(−)-3-methyl-2-phenylbutylamine (3.92 g, 24 mmol), 0.45 equivalent based on the amount of (±)-2-(3-benzoylphenyl)propionic acid, was added dropwise with stirring at 40°C. After completing the addition, the reaction solution was stirred at 40°C. for 2 hours, followed by stirring at room temperature for 6 hours and then at 10°C. for 2 hours. Then, the crystal precipitated was filtered, and the filter cake was washed with cold MIBK (25 ml) and dried to give a diastereomer salt (6.48 g) of (R)-(−)-2-(3-benzoylphenyl)propionic acid with (R)-(−)-3-methyl-2-phenylbutylamine. The yield of the product based on (R)-2-(3-benzoylphenyl)propionic acid contained in the starting material was 58.3%.

To this diastereomer salt, excess diluted hydrochloric acid was added and the mixture was stirred for a while. Then, (R)-(−)-2-(3-benzoylphenyl)propionic acid liberated was extracted with ethyl acetate, and the extract solution was washed with water and dried over magnesium sulfate. The solvent was distilled off under reduced pressure, and hexane was then added to allow crystallization. After cooling, the crystal was filtered off and dried to give (R)-(−)-2-(3-benzoylphenyl)propionic acid (3.73 g). The yield of the product based on (R)-(−)-2-(3-benzoylphenyl)propionic acid contained in the starting material was 55% and the optical purity was 98.6% e.e. $[\alpha]_D^{25}$=−45.7° (c=1, methyl alcohol).

Example 3

(±)-2-(3-Benzoylphenyl)propionic acid (12.7 g, 50 mmol) was added to MIBK (70 ml) and dissolved with heating to 35° C. Then, (S)-(+)-3-methyl-2-phenylbutylamine (5.24 g, 32 mmol) was added dropwise with stirring. After completing the addition, the reaction solution was stirred at 35° C. to 40° C. for one hour, followed by at room temperature for 5 hours and then at 10° C. for 2 hours. Then, the crystal precipitated was filtered, and the filter cake was washed with cold MIBK (30 ml) and dried to give a diastereomer salt (8.76 g) of (S)-(+)-2-(3-benzoylphenyl)propionic acid with (S)-(+)-3-methyl-2-phenylbutylamine. The yield of the product based on (S)-(+)-2-(3-benzoylphenyl)propionic acid contained in the starting material was 84%.

This diastereomer salt was recrystallized from IPA (97 ml) to give a purified diastereomer salt (7.42 g). Purification yield: 84.7%. Melting point: 133–135.5° C.

To this purified diastereomer salt, 15% (w/v) hydrochloric acid (30 g) was added and the mixture was stirred for a while. Then, (S)-(+)-2-(3-benzoylphenyl)propionic acid liberated was extracted with ethyl acetate, and the extract solution was washed with water and dried over magnesium sulfate. The solvent was distilled off under reduced pressure, and hexane was then added to allow crystallization. After cooling, the crystal was filtered and dried to give (S)-(+)-2-(3-benzoylphenyl) propionic acid (5.6 g). The yield of the product based on (S)-(+)-2-(3-benzoylphenyl)propionic acid contained in the starting material was 55.2% and the optical purity was 99.7% e.e. Melting point: 77–78.5°C. $[\alpha]_D^{25}$=+45.7° (c=1, methyl alcohol).

Example 4

(±)-2-(3-Benzoylphenyl)propionic acid (12.7 g, 50 mmol) was added to methyl ethyl ketone (hereinafter abbreviated to "MEK") (70 ml) and dissolved with heating. Then, (S)-(+)-3-methyl-2-phenylbutylamine (4.9 g, 30 mmol) was added dropwise with stirring. After completing the addition, the reaction solution was stirred at 35°C. to 40°C. for one hour and then at room temperature for 4 hours, and finally maintained at 10°C. for 3 hours. The crystal precipitated was filtered, and the filter cake was washed with cold MEK (35 ml) and dried to give a diastereomer salt (7.72 g) of (S)-(+)-2-(3-benzoylphenyl) propionic acid with (S)-(+)-3-methyl-2-phenylbutylamine. The yield of the product based on (S)-(+)-2-(3-benzoylphenyl) propionic acid contained in the starting material was 74%.

This diastereomer salt was recrystallized from IPA (77 ml). That is, the diastereomer salt was dissolved in IPA (77 ml) with heating and then cooled slowly to 10°C. The crystal precipitated was filtered and washed with cold IPA to give a purified diastereomer salt (6.48 g). Purification yield: 83.9%. Melting point: 134.5–135.5° C.

This purified diastereomer salt was added to 15% (w/v) hydrochloric acid (40 ml) and the mixture was stirred for a while. Then, (S)-(+)-2-(3-benzoylphenyl)propionic acid liberated was extracted with ethyl acetate, and the extract solution was washed with water and dried over magnesium sulfate. The solvent was distilled off under reduced pressure, and hexane was then added to allow crystallization. After cooling, the crystal was filtered and dried to give (S)-(+)-2-(3-benzoylphenyl)propionic acid (3.73 g). The yield was 94.5%. The yield of the product based on (S)-(+)-2-(3-benzoylphenyl)propionic acid contained in the starting material was 58.7% and the optical purity was 99.5% e.e. Melting point: 77°–78° C. $[\alpha]_D^{25}$=+45.5° (c=1, methyl alcohol).

Example 5

(±)-2-(3-Benzoylphenyl)propionic acid (12.7 g, 50 mmol) was added to tetrahydrofuran (hereinafter abbreviated to "THF") (45 ml) and dissolved. Then, (S)-(+)-3-methyl-2-phenylbutylamine (4.1 g, 25 mmol) was added dropwise with stirring. After completing the addition, the reaction solution was maintained at 35° C. to 40° C. for one hour, stirred at room temperature for 4 hours, and then cooled to 10° C. The crystal precipitated was filtered, and the filter cake was washed with cold THF (35 ml) and then dried to give a diastereomer salt (5.84 g) of (S)-(+)-2-(3-benzoylphenyl)propionic acid with (S)-(+)-3-methyl-2-phenylbutylamine. The yield of the product based on (S)-(+)-2-(3-benzoylphenyl)propionic acid contained in the starting material was 56% and the optical purity was 94.3% e.e.

In the same manner as described above, (±)-2-(3-benzoylphenyl)propionic acid was reacted with (S)-(+)-3-methyl-2-phenylbutylamine at various molar ratios in various organic solvents. The yield and optical purity of the diastereomer salt obtained by this reaction are as shown in Table 2 below. In Table 2, (±)-2-(3-benzoylphenyl)propionic acid and (S)-(+)-3-methyl-2-phenylbutylamine are abbreviated to (±)-KET and (S)-PBA, respectively. Furthermore, the E value was calculated according to the following equation and it was taken as an index for evaluation.

E value=(yield of diastereomer salt×optical purity)/100.

TABLE 2

| Solvent | Solvent ml/(±)-KET g | Molar ratio (S)-PBA/ (±)-KET | Yield of diastereomer salt (%) | Optical purity (% e.e.) | E value |
|---|---|---|---|---|---|
| MIBK | 5.5 | 0.45 | 55.8 | 97.4 | 54.35 |
| MIBK | 6.2 | 0.5 | 69.0 | 97.8 | 67.48 |
| MIBK | 5.5 | 0.6 | 79.6 | 94.0 | 74.82 |
| MIBK | 6.3 | 0.64 | 84.0 | 93.0 | 78.12 |
| MEK | 3.5 | 0.6 | 74.0 | 96.0 | 71.04 |
| MEK | 3.6 | 0.7 | 87.4 | 88.8 | 77.61 |
| Ethyl acetate | 3.5 | 0.5 | 60.4 | 93.2 | 56.29 |
| IPA | 3.6 | 0.5 | 66.9 | 9p.3 | 59.60 |
| THF | 3.5 | 0.5 | 56.0 | 94.3 | 52.81 |
| Toluene + Ethyl acetate | 2.4 + 1.7 | 0.6 | 76.7 | 91.7 | 70.33 |

Example 6

Firstly, from (±)-2-(3-benzoylphenyl)propionic acid, (S)-(+)-2-(3-benzoylphenyl)propionic acid was isolated as a diastereomer salt using (S)-(+)-3-methyl-2-phenylbutylamine. Then, from the mother filtrate, (R)-(−)-2-(3-benzoylphenyl)propionic acid was obtained using (R)-(−)-3-methyl-2-phenylbutylamine.

That is, (±)-2-(3-benzoylphenyl)propionic acid (12.7 g, 50 mmol) was dissolved in MIBK (76 ml) and (S)-(+)-3-methyl-2-phenylbutylamine (4.9 g, 30 mmol) was added dropwise at 40° C. This reaction solution was stirred at 35° C. to 40° C. for one hour, followed by at room temperature for 5 hours and then at 10° C. to 15° C. for one hour. Then, the crystal precipitated was filtered, and the filter cake was washed with cold MIBK (30 ml) and dried to give a diastereomer salt (8.34 g) of (S)-(+)-2-(3-benzoylphenyl)propionic acid with (S)-(+)-3-methyl-2-phenylbutylamine. The yield of the product based on (S)-(+)-2-(3-benzoylphenyl)propionic acid contained in the starting material was 80%. Melting point: 129°–131° C. Optical purity: 94.3% e.e.

The above filtrate was combined with the washed solution, 15% (w/v) sulfuric acid (20 ml) was added to the combined solution, and the mixture was then stirred for 20 minutes. After the mixture was subjected to phase separation, the organic layer was taken and washed with water and dried over magnesium sulfate. The solution was concentrated to 68 g by weight by evaporating the solvent under reduced pressure. To this concentrated solution, (R)-(−)-3-methyl-2- phenylbutylamine (4.25 g, 25.8 mmol), 1.03 equivalents based on the amount of (R)-(−)-2-(3-benzoylphenyl)propionic acid contained in the starting material, was added dropwise with stirring at 40° C. After completing the addition, the reaction solution was stirred at 35° C. to 40° C. for one hour, followed by at room temperature for 5 hours and then at 10° C. to 15° C. for 1.5 hours. Then, the crystal precipitated was filtered, washed with cold MIBK (30 ml) and then dried to give a diastereomer salt (8.91 g) of (R)-(−+)-2-(3-benzoylphenyl)propionic acid with (R)-(−)-3-methyl-2-phenylbutylamine. The yield of the product based on (R)-(−)-2-(3-benzoylphenyl)propionic acid contained in the starting material [(±)-2-(3-benzoylphenyl)propionic acid] was 85.5%. Melting point: 133°–134.5° C. Optical purity: 95.2% e.e. Then, (R)-(−)-2-(3-benzoylphenyl)propionic acid was isolated from this crude diastereomer salt using hydrochloric acid. Melting point: 75.5°–77.5° C. $[\alpha]_D^{25}$=−45.0° (c =1, methyl alcohol).

The above crude diastereomer salt (7.8 g) of (R)-(−)-2-(3-benzoylphenyl)propionic acid with (R)-(−)-3-methyl-2-phenylbutylamine was recrystallized from IPA (88 ml) to give a purified diastereomer salt (6.7 g). The purification yield was 85.9%. Melting point: 133.5°–135° C. Then, (R)-(−)-2-(3-benzoylphenyl)propionic (4.08 g) was isolated from this purified diastereomer salt using 15% (w/v) hydrochloric acid. Melting point: 77°–78.5° C. $[\alpha]_D^{25}$=−47.20° (c=1, methyl alcohol). Optical purity: 99.6% e.e. The yield of the product based on (R)-(−)-2-(3-benzoylphenyl)propionic acid contained in the starting material was 73.4%.

Example 7

(±)-2-(3-Benzoylphenyl)propionic acid (51 g, 0.2 mol) was dissolved in MIBK (290 ml) and (S)-(+)-3-methyl-2-phenylbutylamine (19.6 g, 0.12 mol) was added dropwise with stirring. After completing the addition, the reaction solution was maintained at 35° C. to 40° C. for one hour and stirred at room temperature for 5 hours and then at 10° C. for 3 hours. Then, the crystal precipitated was filtered and the filter cake was washed with cold MIBK (70 ml) to give a wet cake (67 g). To this wet cake was added MIBK (240 ml) and the mixture was heated to dissolve at 77° C. Then, the mixture was cooled and stirred at 10° C. for 2 hours. Then, the crystal precipitated was filtered to give a diastereomer salt (30.2 g) of (S)-(+)-2-(3-benzoylphenyl)propionic acid with (S)-(+)-3-methyl-2-phenylbutylamine. This diastereomer salt was treated with hydrochloric acid to give (S)-(+)-2-(3-benzoylphenyl)propionic acid (18.26 g). The optical purity of this propionic acid was 99.2% e.e. The yield of the product based on (S)-(+)-2-(3-benzoylphenyl)propionic acid contained in the starting material was 71.6% e.e.

Example 8

To (±)-2-(3-benzoylphenyl)propionic acid (1200 g, 4.719 mol) were added methyl-t-butyl ether (hereinafter abbreviated to "MTBE") (4.8 L) and water (600 g, water/KET= 0.50) and the mixture was dissolved with heating. Then, (S)-(+)-3-methyl-2-phenylbutylamine (388 g, 2.377 mol) was added dropwise with stirring at 50° C. to 55° C. This reaction solution was cooled to precipitate a crystal and then reheated from 35° C. to 50° C. This solution was again cooled and then reheated from 40° C. to 45° C. This solution was cooled slowly to 10° C. and stirred at 5° C. to 10° C. for one hour. Then, the crystal precipitated was filtered, and the filter cake was washed three times with cold MTBE (1 L) and dried. In this manner, a diastereomer salt (741 g, 1.775 mol) of (S)-(+)-2-(3-benzoylphenyl)propionic acid with (S)-(+)-3-methyl-2-phenylbutylamine was obtained. The yield of the product based on (S)-(+)-2-(3-benzoylphenyl)propionic acid contained in the starting material was 75.2% and the optical purity was 99.1% e.e.

This diastereomer salt (720 g, 1.724 mol) was added to 4% (w/v) hydrochloric acid (2279 g) and dissolved with heating to 50° C. This solution was cooled to precipitate a crystal and water (0.79 L) was then added at 15° C. This solution was again cooled to 10° C., stirred at 5° C. to 10° C. for 2 hours and then filtered. This filter cake was washed three times with water (1 L) and dried to give crude (S)-(+)-2-(3-benzoylphenyl)propionic acid (431 g, 1.695 mol). The yield was 98.3%. The total yield of the product based on (S)-(+)-2-(3-benzoylphenyl)propionic acid contained in the starting material was 73.9% and the optical purity was 99.4% e.e. Melting point: 76.8–77.4° C. $[\alpha]_D^{25}$= +46.29 (c=1, methyl alcohol).

In the same manner as described above except that the amount of water to be used for (±)-2-(3-benzoylphenyl) propionic acid was changed, (±)-2-(3-benzoylphenyl) propionic acid was reacted with (S)-(+)-3-methyl-2-phenylbutylamine. The yield and optical purity of the diastereomer salt obtained by this reaction are as shown in Table 3 below. In Table 3, (±)-2-(3-benzoylphenyl)propionic acid is abbreviated to (±)-KET. Furthermore, the E value was calculated according to the following equation and it was taken as an index for evaluation.

E value=(yield of diastereomer salt×optical purity)/100.

TABLE 3

| Amount of water to be added water/KET (w/w) | Yield of diastereomer salt (%) | Optical purity (% e.e) | E value |
|---|---|---|---|
| 0.75 | 74.8 | 89.10 | 66.65 |
| 0.60 | 73 | 90.10 | 65.77 |
| 0.55 | 75 | 97.80 | 73.35 |
| 0.50 | 75.2 | 99.1 | 74.52 |
| 0.45 | 75.2 | 98.90 | 74.37 |
| 0.40 | 75.8 | 97.00 | 73.53 |
| 0.20 | 73 | 96.90 | 70.74 |
| 0.00 | 85.2 | 77.30 | 65.86 |

As is apparent from Table 3, a high optical purity and E value can be obtained when water is used in the proportion of 0.10 to 0.60% (w/w), preferably 0.20 to 0.55% (w/w), to (±)-2-(3-benzoylphenyl)propionic acid.

Reference Example 1

In the same manner as described in Example 6, a diastereomer salt of (S)-(+)-2-(3-benzoylphenyl)propionic acid with (S)-(+)-3-methyl-2-phenylbutylamine was obtained from (±)-2-(3-benzoylphenyl)propionic acid. The filtrate obtained after filtering off the crystal of the diastereomer salt was combined with the washed solution of the crystal, and 15% (w/v) sulfuric acid (20 ml) was added to the combined solution. The mixture was then stirred for 20 minutes. After the mixture was subjected to phase separation, the organic layer was taken and washed with water and dried over magnesium sulfate. The solvent was evaporated to dryness under reduced pressure to give 2-(3-benzoylphenyl) propionic acid (7.62 g, 30 mmol) rich in (R)-isomer.

To this was added methyl alcohol (8 ml), followed by potassium hydroxide (3.36 g, 60 mmol), and racemization was conducted by heating the mixture under reflux for 2 hours. To this reaction solution were added water (40 ml) and 35% (w/v) hydrochloric acid (6.79 g, 66 mmol) and the mixture was cooled to 10° C. to precipitate a crystal. The crystal was filtered, and the filter cake was washed with water (10 ml) and dried to give a racemate (7.54 g, 29.7 mmol). The yield was 99.0% and optical purity was 0% e.e.

Example 9

To (±)-2-(3-benzoylphenyl)propionic acid (7.0 g, 27.5 mmol) obtained in Reference Example 1 were added MTBE (28 ml) and water (3.2 ml, water/KET=0.46) and the mixture was dissolved with heating. Then, (S)-(+)-3-methyl-2-phenylbutylamine (2.5 g, 13.75 mmol) was added dropwise with stirring at 50° C. to 55° C. This reaction solution was cooled to precipitate a crystal and then reheated from 35° C. to 50° C. Again, this solution was cooled and reheated from 40° C. to 45° C. This solution was cooled slowly to 10° C. and stirred at 5°C. to 10° C. for one hour. Then, the crystal precipitated was filtered, and the filter cake was washed three times with cold MTBE (5 ml) and dried. In this manner, a diastereomer salt (4.3 g, 10.3 mmol) of (S)-(+)-2-(3-benzoylphenyl)propionic acid with (S)-(+)-3-methyl-2-phenylbutylamine was obtained. The yield of the product based on (S)-(+)-2-(3-benzoylphenyl)propionic acid contained in the starting material was 74.9% and the optical purity was 99.0% e.e.

This diastereomer salt was added to 4% (w/v) hydrochloric acid (148 g) and dissolved with heating to 50C. This solution was cooled to precipitate a crystal and water (5 ml) was then added at 15° C. This solution was again cooled to 10° C., stirred at 5° C. to 10° C. for 2 hours and then filtered. This filter cake was washed three times with water (6 ml) and dried to give crude (S)-(+)-2-(3-benzoylphenyl) propionic acid (2.57 g, 10.1 mmol). The yield was 98.1%. The total yield of the product based on (S)-(+)-2-(3-benzoylphenyl)propionic acid contained in the starting material was 73.5% and the optical purity was 98.9% e.e.

As described above, when optically active (S)- or (R)-3-methyl-2-phenylbutylamine is used as an optical resolution agent in the amount of about 0.5 equivalent based on the amount of (±)-2-(3-benzoylphenyl)propionic acid, it is possible to obtain, in a high yield, (S)- or (R)-2-(3-benzoylphenyl)propionic acid, which has an extremely high optical purity of 98% or more, furthermore 99% or more, and which can be applied for practical use as a drug, without any recrystallization step or with only one time of recrystallization step. That is, the present invention provides a practical and efficient process for resolving (±)-2-(3-benzoylphenyl)propionic acid.

Furthermore, when (S)- or (R)-3-methyl-2-phenylbutylamine is used for 2-(3-benzoylphenyl)propionic acid rich in (S)-isomer or (R)-isomer which is recovered from the solution obtained after separating a diastereomer salt, in the amount of about one equivalent based on the amount of (S)-isomer or (R)-isomer contained in the recovered 2-(3-benzoylphenyl)propionic acid, it is possible to obtain (S)- or (R)-2-(3-benzoylphenyl)propionic acid in a still higher yield. That is, a practical and efficient process for producing optically active 2-(3-benzoylphenyl)propionic acid is provided in which both (S)- and (R)-isomers are obtained simultaneously by a series of steps.

What is claimed is:

1. A process for separating (S)- or (R)-2-(3-benzoylphenyl)propionic acid from a mixture of (S)- and (R)-2-(3-benzoylphenyl)propionic acid, which comprises the steps of:

(1) reacting the mixture of (S)- and (R)-2-(3-benzoylphenyl)propionic acid with (S)- or (R)-3-methyl-2-phenylbutylamine in a suitable ether solvent in the presence of water to form a diastereomer salt of (S)-2-(3-benzoylphenyl)propionic acid with (S)-3-methyl-2-phenylbutylamine or a diastereomer salt of (R)-2-(3-benzoylphenyl)propionic acid with (R)-3-methyl-2-phenylbutylamine;

(2) separating the diastereomer salt from the reaction mixture; and (3) liberating the separated diastereomer salt to give (S)- or (R)-2-(3-benzoylphenyl)propionic acid.

2. The process according to claim 1 wherein the mixture of (S)- and (R)-2-(3-benzoylphenyl)propionic acid is a racemic mixture.

3. The process according to claim 1 wherein (S)-2-(3-benzoylphenyl)propionic acid is separated by reacting the mixture of (S)- and (R)-2-(3-benzoylphenyl)propionic acid with (S)-3-methyl-2-phenylbutylamine.

4. The process according to claim 1 wherein (R)-2-(3-benzoylphenyl)propionic acid is separated by reacting the mixture of (S)- and (R)-2-(3-benzoylphenyl)propionic acid with (R)-3-methyl-2-phenylbutylamine.

5. The process according to claim 1 wherein (S)- or (R)-3-methyl-2-phenylbutylamine is used in an amount between about 0.8 and about 1.5 equivalents based on the moles of (S)- or (R)-2-(3-benzoylphenyl)propionic acid contained in the mixture.

6. The process according to claim 1 wherein the solvent is methyl t-butyl ether.

7. The process according to claim 1 wherein the water is present in the reaction mixture in an amount of from 10 to 60% (w/w) based on the amount of the mixture of (S)- and (R)-2-(3-benzoylphenyl)propionic acid.

8. The process according to claim 1 wherein the diastereomer salt is formed at a temperature between room temperature and 40° C.

9. The process according to claim 1 wherein the diastereomer salt separated in step (2) is used in the subsequent liberation step without purifying the salt.

10. The process according to claim 1 wherein the diastereomer salt separated in the step (2) is purified by recrystallization and the purified salt is used in the subsequent liberation step.

11. The process according to claim 10 wherein the solvent for recrystallization is ketones, alcohols, water or a mixed solvent thereof.

12. The process according to claim 1 which comprises the steps of:
   (1) reacting the mixture of (S)- and (R)-2-(3-benzoylphenyl)propionic acid with (S)-3-methyl-2-phenylbutylamine in a suitable ether solvent in the presence of water to form a diastereomer salt of (S)-2-(3-benzoylphenyl)propionic acid with (S)-3-methyl-2-phenylbutylamine;
   (2) separating the diastereomer salt from the reaction mixture;
   (3) optionally purifying the separated diastereomer salt by recrystallization and then liberating the salt to give (S)-2-(3-benzoylphenyl)propionic acid;
   (4) removing (S)-3-methyl-2-phenylbutylamine from the solution obtained after separating the diastereomer salt in the above step (2) to obtain a solution containing 2-(3-benzoylphenyl)propionic acid rich in (R)-isomer;
   (5) adding (R)-3-methyl-2-phenylbutylamine to the solution obtained in the above step (4) to form a diastereomer salt of (R)-2-(3-benzoylphenyl)propionic acid with (R)-3-methyl-2-phenylbutylamine;
   (6) separating the diastereomer salt from the reaction mixture; and
   (7) optionally purifying the separated diastereomer salt by recrystallization and then liberating the salt to give (R)-2-(3-benzoylphenyl)propionic acid.

13. The process according to claim 1 which comprises the steps of:
   (1) reacting the mixture of (S)- and (R)-2-(3-benzoylphenyl)propionic acid with (R)-3-methyl-2-phenylbutylamine in a suitable ether solvent in the presence of water to form a diastereomer salt of (R)-2-(3-benzoylphenyl)propionic acid with (R)-3-methyl-2-phenylbutylamine;
   (2) separating the diastereomer salt from the reaction mixture;
   (3) optionally purifying the separated diastereomer salt by recrystallization and then liberating the salt to give (R)-2-(3-benzoylphenyl)propionic acid;
   (4) removing (R)-3 methyl-2-phenylbutylamine from the solution obtained after separating the diastereomer salt in the above step (2) to obtain a solution containing 2-(3-benzoylphenyl)propionic acid rich in (S)-isomer;
   (5) adding (S)-3-methyl-2-phenylbutylamine to the solution obtained in the above step 4) to form a diastereomer salt of (S)-2-(3-benzoylphenyl)propionic acid with (S) -3-methyl-2-phenylbutylamine;
   (6) separating the diastereomer salt from the reaction mixture; and
   (7) optionally purifying the separated diastereomer salt by recrystallization and then liberating the salt to give (S)-2-(3-benzoylphenyl)propionic acid.

14. The process according to claim 1 wherein the water is present in the reaction mixture in an amount of from 10 to 60% (w/w) based on the amount of the mixture of (S)- and (R)-2-(3-benzoylphenyl)propionic acid.

* * * * *